(12) United States Patent
Bassler et al.

(10) Patent No.: US 6,204,408 B1
(45) Date of Patent: Mar. 20, 2001

(54) METHOD FOR SEPARATING 6-AMINOCAPRONITRILE FROM MIXTURES CONTAINING 6-AMINOCAPRONITRILE AND AN IMINE

(75) Inventors: Peter Bassler, Viernheim; Hermann Luyken, Ludwigshafen; Alwin Rehfinger, Mutterstadt; Harald Rust, Neustadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/341,946

(22) PCT Filed: Jan. 17, 1998

(86) PCT No.: PCT/EP98/00243

§ 371 Date: Jul. 21, 1999

§ 102(e) Date: Jul. 21, 1999

(87) PCT Pub. No.: WO98/34911

PCT Pub. Date: Aug. 13, 1998

(30) Foreign Application Priority Data

Feb. 7, 1997 (DE) ............................................. 197 04 620

(51) Int. Cl.[7] .................................................. C07C 255/00

(52) U.S. Cl. ............................................................ 558/452

(58) Field of Search ................................. 558/452; 203/57

(56) References Cited

U.S. PATENT DOCUMENTS

| | | |
|---|---|---|
| 4,389,348 | 6/1983 | Diamond et al. . |
| 4,601,859 | 7/1986 | Galle et al. . |
| 5,133,838 | 7/1992 | Sieja . |
| 5,153,351 | 10/1992 | Sieja . |
| 5,162,567 | 11/1992 | Sieja . |

FOREIGN PATENT DOCUMENTS

| | | |
|---|---|---|
| 42 35 466 | 4/1994 | (DE) . |
| 195 00 222 | 7/1996 | (DE) . |
| 195 48 289 | 6/1997 | (DE) . |
| 77 911 | 5/1983 | (EP) . |
| 161 419 | 11/1985 | (EP) . |
| 497 333 | 8/1992 | (EP) . |
| 93/01207 | 1/1993 | (WO) . |

Primary Examiner—Joseph K. McKane
Assistant Examiner—Joseph Murray
(74) Attorney, Agent, or Firm—Keil & Weinkauf

(57) ABSTRACT

A process for distillative removal of 6-aminocapronitrile from mixtures (I) comprising 6-aminocapronitrile and an imine (II) comprises conducting the distillation in the presence of carbon dioxide.

9 Claims, No Drawings

METHOD FOR SEPARATING 6-AMINOCAPRONITRILE FROM MIXTURES CONTAINING 6-AMINOCAPRONITRILE AND AN IMINE

The instant application is a 371 of PCT/EP98/00243 filed Jan. 17, 1998.

DESCRIPTION

The present invention relates to a process for distillative removal of 6-aminocapronitrile from mixtures (I) comprising 6-aminocapronitrile and an imine (II).

The partial hydrogenation of adiponitrile to 6-aminocapronitrile in the presence of a catalyst based on a metal such as nickel, cobalt, iron, rhodium or ruthenium is generally known, for example from EP-A-161 419, EP-A-77 911, U.S. Pat. No. 4,389,348, U.S. Pat. No. 4,601,859, WO 93/1207, DE-A 42 35 466, DE-A 19 500 222 and German Application 19 548 289.1.

Byproducts include imines, especially tetrahydroazepine (THA) of the formula

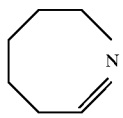

6-Aminocapronitrile is chiefly used for fiber production via caprolactam as intermediate or by direct polymerization to nylon-6. For this, the 6-aminocapronitrile has to be very pure, in which connection it is known that the removal of THA presents problems.

U.S. Pat. No. 5,162,567 discloses reacting a mixture comprising 6-aminocapronitrile and THA with an organic carbonyl compound, for example a ketone or an aldehyde, at high temperature and then removing 6-aminocapronitrile from the mixture. U.S. Pat. No. 5,153,351 discloses reacting a mixture comprising 6-aminocapronitrile and THA with an organic active-CH methylene compound, for example malonitrile, cyclopentadiene, nitromethane or nitroethane, and then removing 6-aminocapronitrile from the mixture. The disadvantage for these processes is that the addition of a further organic compound to the mixture makes it more difficult to prepare pure 6-aminocapronitrile.

In U.S. Pat. No. 5,133,838, a mixture comprising 6-aminocapronitrile and THA is reacted with an inorganic hydride such as lithium borohydride. Disadvantageously, in this process, the hydride has to be used in a multiple excess of the stoichiometrically required quantity. In addition, care has to be taken in the subsequent distillation not to hydrogenate the product of value, 6-aminocapronitrile.

EP-A-497 333 describes a process whereby a mixture comprising 6-aminocapronitrile and THA is reacted with an alkaline compound. Disadvantageously, the alkaline compound has to be used in excess of the stoichiometrically required quantity and the 6-aminocapronitrile has to be distilled out of the resulting reaction mixture at greatly reduced pressure.

It is an object of the present invention to provide a technically simple and economical process for removing 6-aminocapronitrile from a mixture comprising essentially 6-aminocapronitrile and THA by overcoming the aforementioned disadvantages.

We have found this object is achieved by a process for distillative removal of 6-aminocapronitrile from mixtures (I) comprising 6-aminocapronitrile and an imine (II), which comprises conducting the distillation in the presence of carbon dioxide.

Mixtures (I) are obtainable in a conventional manner by partial hydrogenation of ADN, for example according to a process as described in EP-A-161 419, EP-A-77 911, U.S. Pat. No. 4,389,348, U.S. Pat. No. 4,601,859, WO 93/1207, DE-A 42 35 466, DE-A 19 500 222 and German Application 19 548 289.1, by, in general, conducting the hydrogenation in the presence of nickel-, cobalt-, iron-, rhodium- or ruthenium-containing catalysts. The catalysts can be used as supported or unsupported catalysts. Catalyst supports include for example aluminum oxide, silicon dioxide, titanium dioxide, magnesium oxide, activated carbons and spinels. Examples of unsupported catalysts are Raney nickel and Raney cobalt.

The hydrogenation affords a mixture comprising 6-aminocapronitrile, HMD and an imine (II) with or without ADN. From this mixture it is possible to obtain a mixture (I) comprising essentially 6-aminocapronitrile and an imine (II), for example by distillation.

An imine (II) is suitably selected from aromatic, preferably aliphatic, such as acyclic or especially cyclic, imines and also mixtures thereof, particularly preferably THA.

Imines (II) can be present in mixture (I) as individual compounds or as adducts, for example with amines such as 6-aminocapronitrile, in which case these adducts are herein likewise embraced by imines (II).

Carbon dioxide can be added to the distillation mixture before or preferably during the distillation in the form of a compound which releases carbon dioxide under the distillation conditions, such as ammonium carbonate, ammonium carbamate or urea or mixtures thereof, in which case these compounds can be added in pure form or in a liquid diluent, as in one or more constituents of mixture (I), or in the form of solid, liquid or preferably gaseous carbon dioxide, for example in the form of a gas comprising carbon dioxide, or especially in the form of pure gaseous carbon dioxide which comprises only the customary impurities.

The carbon dioxide content of the distillation mixture should advantageously be within the range from 0.1 to 1 mol of carbon dioxide per mole of imine function of imine (II).

In general, from 0.022 to 0.22 standard $m^3$ per kg of imine are contemplated for this purpose.

Suitable distillation apparatus includes any customary apparatus, as described for example in: Kirk-Othmer, Encyclopedia of Chemical Technology, 3rd Ed., Vol. 7, John Wiley & Sons, New York, 1979, pages 870–881, such as valve plate columns, sieve plate columns, or columns packed with dumped or arranged packing.

The distillation is advantageously conducted within the range from 10 to 100 mbar, preferably within the range from 20 to 50 mbar.

EXAMPLES

6-Aminocapronitrile having the THA contents (% by weight, based on the mixture) as per the table was subjected to a batchwise fractional distillation in a distillation column (diameter 43 mm, height 2.4 m, Sulzer CY fabric packing, 22 theoretical plates) at a reflux ratio of 5:1. The purified 6-aminocapronitrile was obtained as distillate. The results are reported in Table 1.

|  | Inv.Ex. 1 | Inv.Ex. 2 | Inv.Ex. 3 | Comp.Ex. 1 | Comp.Ex. 2 |
|---|---|---|---|---|---|
| THA content of 6-aminocapronitrile, % | 1.97 | 0.87 | 0.86 | 1.8 | 1.81 |
| Crude 6-aminocapronitrile charge, in g | 1502 | 1487 | 1503 | 1440 | 1494 |
| Pressure [mbar] | 20 | 20 | 20 | 50 | 20 |
| Bottom temp. [° C.] | 136 | 135 | 136 | 148 | 137 |
| Carbon dioxide feed standard l/h | 5 | 8 | 10 | 0 | 0 |
| THA content |  |  |  |  |  |
| Distillate % | 0.7 | 0.27 | 0.24 | 1.3 | 1.4 |
| Reduction % | 66 | 69 | 72 | 28 | 22 |
| Bottom product % | 18 | 8.7 | 11.7 | 9.5 | 6.3 |
| Distillate in g | 1389 | 1454 | 1434 | 1246 | 1351 |
| Bottom product in g | 111 | 33 | 33 | 100 | 136 |

We claim:

1. A process for distillative removal of 6-aminocapronitrile from mixtures (I) comprising 6-aminocapronitrile and an imine (II), which comprises conducting the distillation in the presence of carbon dioxide.

2. A process as claimed in claim 1, wherein imine (II) is a cyclic imine.

3. A process as claimed in claim 1, wherein imine (II) is tetrahydroazepine.

4. A process as claimed in claim 1, wherein the carbon dioxide content of the distillation mixture is within the range from 0.1 to 1 mol of carbon dioxide per mole of imine function of imine (II).

5. A process as claimed in claim 1, wherein a gas comprising carbon dioxide is introduced into the bottom region of a distillation column.

6. A process as claimed in claim 1, wherein the distillation is conducted within the range from 10 to 100 mbar.

7. A process as claimed in claim 1, wherein the distillation mixture has added to it a compound (III) which releases carbon dioxide under the distillation conditions.

8. A process as claimed in claim 1, wherein compound (III) is urea, ammonium carbonate, ammonium carbamate or a mixture thereof.

9. A process as claimed in claim 6, wherein the distillation is conducted within the range from 20 to 50 mbar.

* * * * *